(12) United States Patent
Bondice et al.

(10) Patent No.: US 11,944,416 B2
(45) Date of Patent: Apr. 2, 2024

(54) PHOTOPLETHYSMOGRAPHY (PPG) APPARATUS AND METHOD FOR DETERMINING PHYSIOLOGICAL CHANGES

(71) Applicant: Nitto Denko Corporation, Osaka (JP)

(72) Inventors: Estanislao Glenn Bondice, Singapore (SG); Suppasit Chuwatsawat, Singapore (SG); Wiputpong Klinsukon, Singapore (SG); Somchai Baotong, Singapore (SG); Visit Thaveeprungsriporn, Singapore (SG)

(73) Assignee: Nitto Denko Corporation (JP)

( * ) Notice: Subject to any disclaimer, the term of this patent is extended or adjusted under 35 U.S.C. 154(b) by 464 days.

(21) Appl. No.: 16/633,896

(22) PCT Filed: Jul. 26, 2018

(86) PCT No.: PCT/SG2018/050375
§ 371 (c)(1),
(2) Date: Jan. 24, 2020

(87) PCT Pub. No.: WO2019/022670
PCT Pub. Date: Jan. 31, 2019

(65) Prior Publication Data
US 2020/0329986 A1 Oct. 22, 2020

(30) Foreign Application Priority Data
Jul. 26, 2017 (SG) .............. 10201706109Y

(51) Int. Cl.
*A61B 5/00* (2006.01)
*A61B 5/024* (2006.01)

(52) U.S. Cl.
CPC ...... *A61B 5/02427* (2013.01); *A61B 5/02416* (2013.01); *A61B 5/7225* (2013.01);
(Continued)

(58) Field of Classification Search
CPC ... A61B 5/02427; A61B 5/7225; A61B 5/725; A61B 2560/0209; A61B 2562/0233;
(Continued)

(56) References Cited

U.S. PATENT DOCUMENTS 4,444,498 A 4/1984 Heinemann
5,396,893 A * 3/1995 Oberg ................ A61B 5/02416
600/479

(Continued)

FOREIGN PATENT DOCUMENTS

CN 101484065 A 7/2009
CN 104274167 A 1/2015
(Continued)

OTHER PUBLICATIONS

International Search Report for Application No. PCT/SG2018/050375, dated Dec. 17, 2018, pp. 1-3.
(Continued)

*Primary Examiner* — Colin T. Sakamoto
*Assistant Examiner* — Tommy T Ly
(74) *Attorney, Agent, or Firm* — Lerner David LLP

(57) ABSTRACT

Disclosed is a photoplethysmography (PPG) apparatus (100) for determining physiological changes, comprising: a light source to emit alight signal having a variable intensity dependent on a skin characteristic; first and second photodetectors (130) operable to detect a reflection of the light signal to provide a combined current signal; and a signal processing circuit operable to convert the current signal into a PPG signal for determining the physiological changes.

20 Claims, 10 Drawing Sheets

(52) U.S. Cl.
CPC ...... *A61B 5/725* (2013.01); *A61B 2560/0209* (2013.01); *A61B 2562/0233* (2013.01)

(58) Field of Classification Search
CPC . A61B 5/0261; A61B 5/02141; A61B 5/0077; A61B 5/02416
See application file for complete search history.

(56) References Cited

U.S. PATENT DOCUMENTS

| | | | |
|---|---|---|---|
| 5,830,137 A | 11/1998 | Scharf | |
| 7,738,935 B1 | 6/2010 | Turcott | |
| 2002/0042558 A1* | 4/2002 | Mendelson | A61B 5/1455 600/323 |
| 2008/0214903 A1 | 9/2008 | Orbach | |
| 2009/0306487 A1 | 12/2009 | Crowe et al. | |
| 2012/0179011 A1* | 7/2012 | Moon | A61B 5/25 600/324 |
| 2012/0253141 A1 | 10/2012 | Addison et al. | |
| 2013/0211213 A1 | 8/2013 | DeHennis et al. | |
| 2013/0296665 A1 | 11/2013 | Kassim et al. | |
| 2013/0324809 A1* | 12/2013 | Lisogurski | A61B 5/14552 600/323 |
| 2014/0243622 A1 | 8/2014 | Crowe et al. | |
| 2014/0275850 A1 | 9/2014 | Venkatraman et al. | |
| 2014/0275852 A1 | 9/2014 | Hong et al. | |
| 2014/0358012 A1 | 12/2014 | Richards et al. | |
| 2015/0109124 A1 | 4/2015 | He et al. | |
| 2015/0196239 A1 | 7/2015 | Meehan et al. | |
| 2015/0238099 A1 | 8/2015 | Terumoto | |
| 2015/0366513 A1 | 12/2015 | Terumoto | |
| 2016/0081626 A1* | 3/2016 | Takahashi | A61B 5/7225 600/479 |
| 2016/0113526 A1* | 4/2016 | Nageshwar | A61B 5/7278 600/407 |
| 2016/0206221 A1 | 7/2016 | Kim et al. | |
| 2016/0331329 A1 | 11/2016 | Hiroshima et al. | |
| 2017/0014040 A1 | 1/2017 | Shim et al. | |
| 2017/0055860 A1 | 3/2017 | Vermeulen et al. | |
| 2017/0095156 A1 | 4/2017 | Richards | |
| 2017/0095211 A1 | 4/2017 | Wang et al. | |
| 2017/0099711 A1 | 4/2017 | Polley et al. | |
| 2017/0105638 A1* | 4/2017 | Kulach | A61B 5/721 |
| 2017/0156650 A1* | 6/2017 | Bower | A61B 5/14552 |
| 2017/0202465 A1 | 7/2017 | Bartling | |
| 2017/0238826 A1* | 8/2017 | Finlinson | H03K 5/003 |
| 2018/0344255 A1* | 12/2018 | Orron | A61B 5/02438 |

FOREIGN PATENT DOCUMENTS

| | | | |
|---|---|---|---|
| CN | 105326480 A | * | 2/2016 |
| CN | 106456021 A | | 2/2017 |
| CN | 106560156 A | | 4/2017 |
| CN | 106618504 A | * | 5/2017 |
| JP | 2008532587 A | | 8/2008 |
| JP | 200966042 A | | 4/2009 |
| JP | 2015502197 A | | 1/2015 |
| JP | 2015157020 A | | 9/2015 |
| JP | 2016538097 A | | 12/2016 |
| WO | 2017007546 A1 | | 1/2017 |

OTHER PUBLICATIONS

Extended European Search Report including Written Opinion for Application No. EP18837369.0, dated Mar. 29, 2021, pp. 1-12.

* cited by examiner

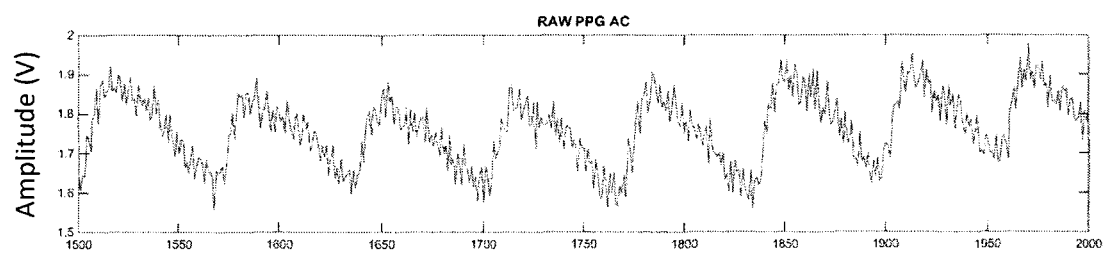
Figure 15(a)    Data point to time domain (12ms/point)
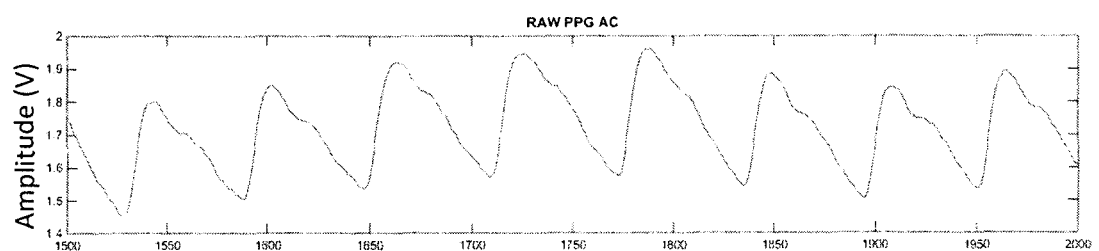
Figure 15(b)    Data point to time domain (12ms/point)

PHOTOPLETHYSMOGRAPHY (PPG) APPARATUS AND METHOD FOR DETERMINING PHYSIOLOGICAL CHANGES

CROSS REFERENCE TO RELATED APPLICATIONS

The present application is a national phase entry under 35 U.S.C. § 371 of International Application No. PCT/SG2018/050375, filed Jul. 26, 2018, which claims priority to Singapore Patent Application No. 10201706109Y, filed Jul. 26, 2017, the disclosures of which are incorporated by reference herein.

TECHNICAL FIELD

The present invention relates to photoplethysmography (PPG) apparatus and method for determining physiological changes.

BACKGROUND

Photoplethysmography (PPG) refers to the use of light to acquire a plethysmogram, which is a volumetric measurement of an organ. PPG is a simple, low-cost technique of detecting blood volume changes in micro-vascular bed of tissues. While PPG is widely used in the medical field for its ease and low-cost of implementation, measurement results obtained using known PPG techniques typically have a low accuracy due the inability of the PPG techniques to effectively handle factors such as user skin tone/colour, user motion, ambient light and ambient temperature. Existing hardware is known to employ complex designs involving complex circuits in order to mitigate these factors.

It is desirable to provide a photoplethysmography (PPG) apparatus and method for determining physiological changes, which address at least one of the drawbacks of the prior art and/or to provide the public with a useful choice.

SUMMARY

According to one aspect, there is provided a photoplethysmography (PPG) apparatus for determining physiological changes, comprising: a light source operable to emit a light signal having a variable intensity dependent on a skin characteristic; first and second photodetectors operable to detect a reflection of the light signal to provide a combined current signal; and a signal processing circuit operable to convert the current signal into a PPG signal for determining physiological changes.

The described embodiments are particularly advantageous. By virtue of the dependency of the intensity of the light signal on the skin characteristic, the light signal can be adjusted to save power or to improve a signal-to-noise ratio of a resultant PPG signal. Further, by using a single light source, a smaller form factor can be achieved. With a single light source, heat generation and power consumption attributed light emission are lower in comparison with existing systems requiring multiple light sources. Furthermore, a smaller footprint may be achieved by the apparatus without compromising the desired light emittance.

The intensity of the light signal may range from 1900 MCD to 3000 MCD. Preferably, the light source is driven by a driving current ranging from 1 mA to 20 mA to provide the light signal. The skin characteristic may be a skin colour (e.g., dependent on pigmentation or tattoo ink). For a darker skin colour, a higher light intensity may be achieved by an increased driving current to improve the signal-to-noise ratio of the resultant PPG signal. For example, for a darker skin colour, the apparatus may be configured such that the driving current varies within the range from 13 mA to 20 mA to provide the light source. For a lighter skin colour, a lower light intensity may be used by lowering the driving current to thereby save power and to reduce the risk of skin damage due to a higher skin sensitivity to light. The skin characteristic may also be, for example, a skin depth and a skin texture. Skin depth may relate to distribution of hair with respect to skin. Skin texture may relate to changes of elastin attributed to age and gender. The PPG technique allows certain light to penetrate to certain skin depth. There are two variants of the technique. In one variant (transmission), light traversing through a body portion of interest (e.g., finger) is detected. In the other variant (reflection), light reflected by a body portion of interest (e.g., wrist) is detected.

The apparatus may further comprise a low signal transistor associated with the light source. For example, the low signal transistor forms part of or is associated with a driving circuit providing the driving current. The low signal transistor is meant for high resolution of the current.

Preferably, the light source is operable to alternate between ON and OFF states to emit the light signal. Little or no power is consumed by the light source in the OFF state. Further, for the adjustment of the light intensity according to the skin characteristic, a variable driving current for driving the light source may be used, as discussed above.

The signal processing circuit may be configured to provide a passband of 0.6 Hz to 8 Hz for filtering a voltage signal relating to the current signal so as to provide the PPG signal. This particular passband corresponds to a portion of current signal representative of information particularly pertinent to a PPG state.

Preferably, the signal processing circuit includes a high-pass filter (HPF) and a low-pass filter (LPF) cooperating to provide the passband for filtering unwanted frequency components. The signal processing circuit may further include another LPF with a cut-off frequency ranging from 100 Hz to 2000 Hz. The signal processing circuit may further include a voltage follower arranged between the HPF and one of the LPFs. The signal processing circuit may further include an amplifier arranged between the HPF and one of the LPFs.

According to another aspect, there is provided a signal processing circuit configured to provide a passband of 0.6 Hz to 8 Hz for filtering a voltage signal relating to a current signal provided by a photodetector so as to provide a PPG signal.

According to another aspect, there is provided a photoplethysmography (PPG) method for determining physiological changes, comprising: emitting, using a light source, a light signal having a variable intensity dependent on a skin characteristic; detecting, using first and second photodetectors, a reflection of the light signal to provide a combined current signal; and converting, using a signal processing circuit, the current signal into a PPG signal for determining the physiological changes.

According to another aspect, there is provided a photoplethysmography (PPG) monitoring apparatus, comprising: a first signal processor configured to provide a command from a MCU port to a digital-to-analog convertor circuit to communicate with the light driver; at least one light source configured to generate and emit a light signal; a light detector unit having at least two photodetectors configured to retrieve light from the at least one light source, wherein the at least one light source is indicative of a current signal; a second signal processor configured to convert the current signal to a voltage signal; the at least one light source having a light driver configured to a low signal transistor for providing a current control from the light driver to the at least one light source; a third signal processor configured to provide a cut-off frequency.

The apparatus may comprise at least one voltage follower configured to communicate with the second signal processor to maintain a voltage output level.

Preferably, the at least one voltage follower communicates with at least one gain amplifier, wherein the at least one gain amplifier further communicates with the third signal processor to amplify to a desired gain.

The desired gain may be 75 or 150.

Preferably, the cut-off frequency is between 0.6 Hz to 8.0 Hz. The third signal processor may be a band pass filter. The low signal transistor may be a NPN. The at least one light source may be green color.

According to another aspect, there is provided a photoplethysmography (PPG) monitoring method comprising: generating a light signal by a light source unit; observing the light signal by at least two photodetectors, wherein the light signal is indicative of an adsorption of a current signal; and converting the current signal to a voltage signal, wherein an analog signal of the voltage signal processed to amplify and filter the analog signal.

The method may further comprise maintaining a voltage output level of the voltage signal with at least one voltage follower. Preferably, the at least one voltage follower communicates with at least one gain amplifier, amplifying a desired gain with the at least one gain amplifier.

Further comprise converting the current signal to the voltage signal based on a transimpedance amplifier.

It is envisaged that features relating to one aspect may be applicable to the other aspects.

BRIEF DESCRIPTION OF THE DRAWINGS

Example embodiments will now be described hereinafter with reference to the accompanying drawings, wherein like parts are denoted by like reference numerals. Among the drawings:

FIGS. 15(a) and 15(b) show time-domain measurements of a PPG signal without and with a LPF of the apparatus of FIG. 1, respectively;

DETAILED DESCRIPTION

Figure 1:
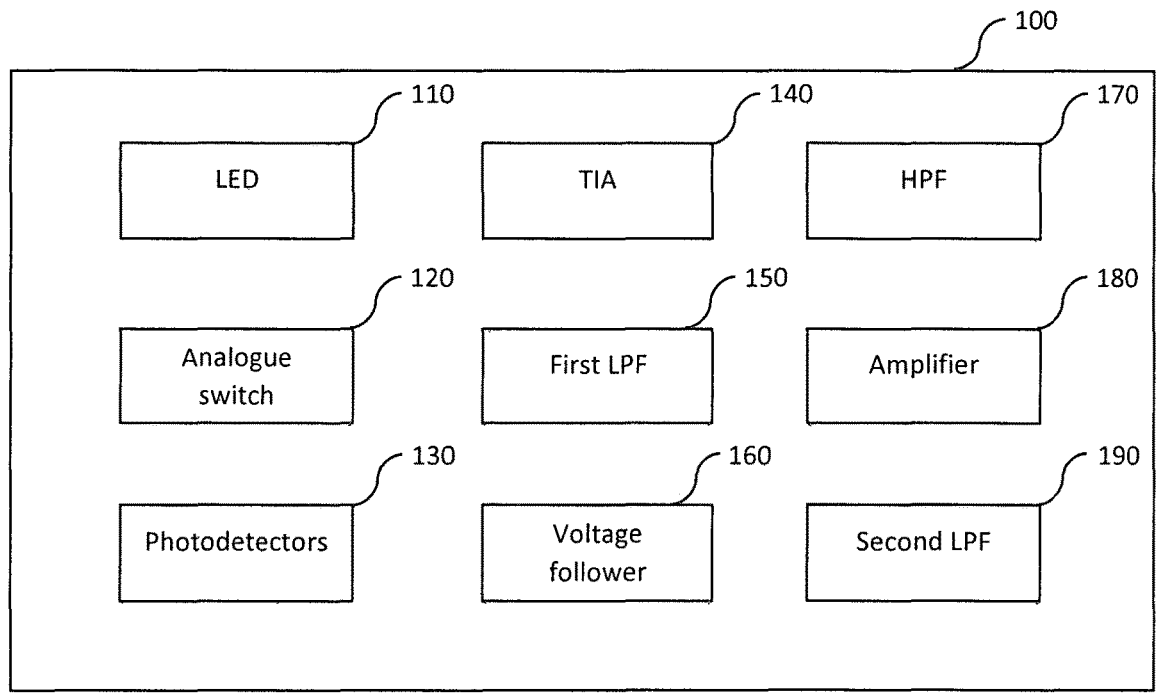
FIG. 1 is a system block diagram of a photoplethysmography (PPG) apparatus for determining physiological changes according an embodiment of the present invention.
Figure 2:
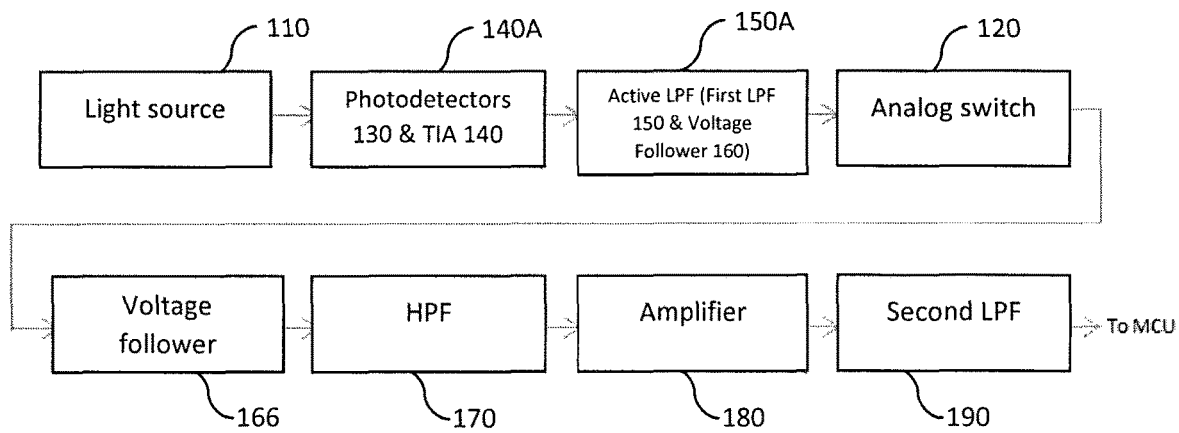
FIG. 2 is a flowchart of signal communication among some components of the apparatus of FIG. 1.
Figure 17:
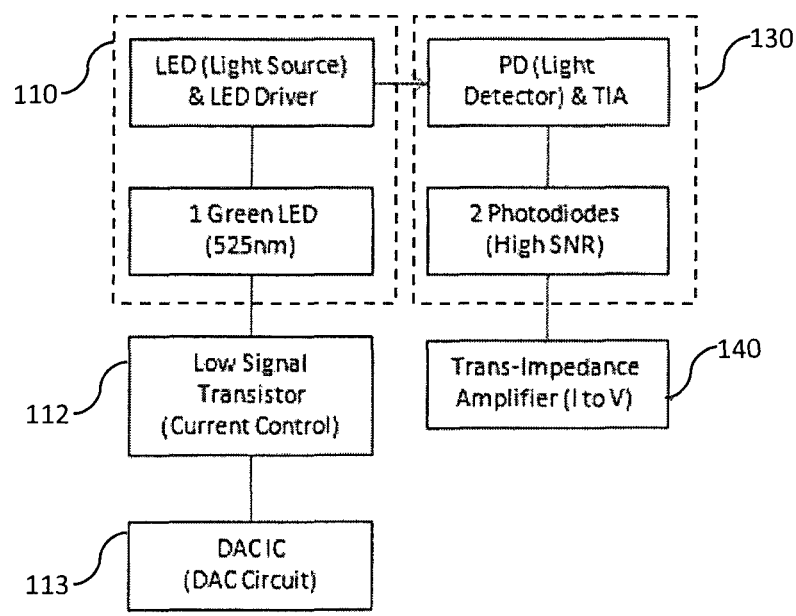
FIG. 17 is another flowchart of signal communication among some components of the apparatus of FIG. 1.

FIG. 1 shows a system block diagram of a photoplethysmography (PPG) apparatus 100 for determining physiological changes according to one embodiment of the present invention. The apparatus 100 includes a light emitting diode (LED) 110, an analogue switch 120, a plurality of photodetectors 130, a transimpedance amplifier (TIA) 140, a first low-pass filter (LPF) 150, a voltage follower 160, a high-pass filter (HPF) 170, an amplifier 180, and a second LPF 190. FIG. 2 illustrates an example flow of signal communication among some of the components 110-190. FIG. 17 illustrates another example flow of signal communication among some of the components 110-190. In this embodiment, the apparatus 100 is wearable on a wrist portion of a user. The components 140-190 form, partially or wholly, a signal processing circuit.

The apparatus 100 can take any suitable form, such as a wearable device (e.g., worn on a wrist) or a non-wearable device. Alternatively, the apparatus 100 may also be implemented in or form part of any suitable device, such as a smartphone device. The apparatus 100 is configured to perform a method for determining physiological changes according to one embodiment of the present invention.

Figure 5:
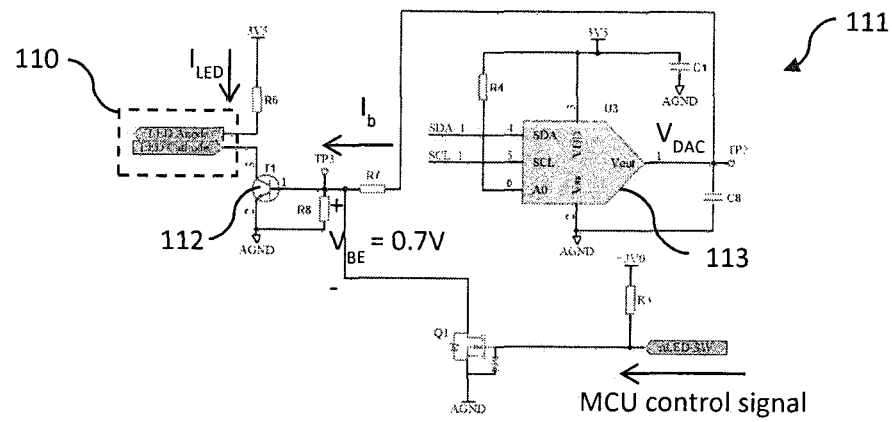
FIG. 5 is a circuit diagram of a driving circuit associated with a light source of the apparatus of FIG. 1.
Figure 6:
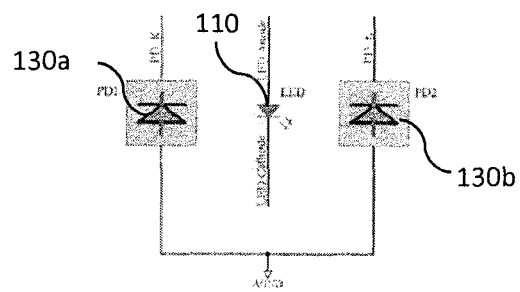
FIG. 6 is a circuit diagram of a pair of photodetectors of the apparatus of FIG. 1.

Referring to FIG. 5, the LED 110, serving as a light source, is driven by a driving current provided by a driving circuit 111 (see the circuit diagram of FIG. 5) to emit a light signal according to a control signal ("MCU control signal") provided by a main communicating unit (MCU, not shown) via a digital-to-analogue converter (DAC) 113 (see also FIG. 17). The emitted light signal has a wavelength between 505 nm to 535 nm, more particularly between 515 nm to 525 nm.

The light signal emitted by the LED 110 has a variable intensity dependent on a skin characteristic of the wrist portion. In this embodiment, the skin characteristic is a skin colour dependent on, for example, skin pigmentation or tattoo ink. The driving current ranges from 1 mA to 20 mA, and the light signal has an intensity correspondingly ranging from 1900 MCD to 3000 MCD. The apparatus 100 is configured such that the variable intensity and hence the driving current are dependent on the skin characteristic. In this embodiment, the darker the skin colour, the higher the driving current. For darker skin colours, the driving current may vary within the range from 13 mA to 20 mA. This arrangement is useful because with a darker skin colour, a larger portion of the emitted light signal is absorbed by the skin, meaning that a smaller portion of the emitted light signal is reflected for detection. By increasing the driving current, the intensity of the light signal can be increased to achieve a resultant PPG signal with a satisfactory signal-to-noise ratio (SNR). Alternatively, with a lighter skin colour, a smaller portion of the emitted light signal is absorbed, meaning that a larger portion of the emitted light signal is reflected. This allows a smaller driving current to be used to achieve a resultant PPG signal with a satisfactory SNR, thereby reducing power consumption.

The LED 110 alternates between ON and OFF states according to the control signal provided by the MCU. At the ON state, the LED 110 emits the light signal with the variable intensity as described above. At the OFF state, the LED 110 emits no light. A low signal transistor 112 associated with the LED 110 is shown to be marked by a circle in FIG. 5. In this embodiment, the low signal transistor 112 forms part of the driving circuit 111 such that the driving circuit 111 further control alternation of the LED between the ON and OFF states in addition controlling the intensity of the emitted light signal. In one example configuration, the ON and OFF states have durations of 1 ms and 11 ms, respectively. The low signal transistor is used to achieve a wider resolution range for the light signal. As described above, the resolution range, with the low signal transistor, typically falls within the range from 1900 MCD to 3000 MCD. With such a configuration, the light signal correspondingly alternates between two intensity states representable by a square wave of two states. In other embodiments, the LED 110 may be controlled to alternate between two ON states of different intensity levels.

With respect to the low signal transistor 112 as shown in FIG. 5, the driving current is marked by "$I_{LED}$" and is controlled by a base current marked by "$I_b$" from the DAC 113. The DC gain of the low signal transistor "$h_{FE}$" satisfies the relationship of $I_{LED}=h_{FE} \times I_b$. The base current flows through the resistor marked by "R7" and is controlled by a voltage (marked by "$V_{DAC}$") the DAC (marked by "U3") and dependent on the MCU control signal. With the voltage difference between the base and emitter being 0.7, the base current satisfies the relationship:

$$I_b = \frac{(V_{DAC} - 0.7)}{R_7}$$

Thus, the driving current is controlled by the base current of the low signal transistor and is a product of the base current and the DC gain value (typically ranging from 100 to 250).

In embodiments of multiple LEDs, where more than one LED needs to be activated at any given time, or where the intensity of the light signal is to be increased, the voltage of the driving signal may be increased from 3.3 V to 3.5 V through a reduction in resistance of an associated resistor (e.g., a fixed resistor) from 3.3 Ohms (Ω) to 1 Ohms (Ω), which results in a change of the driving current from 13 mA to 20 mA.

Figure 7:
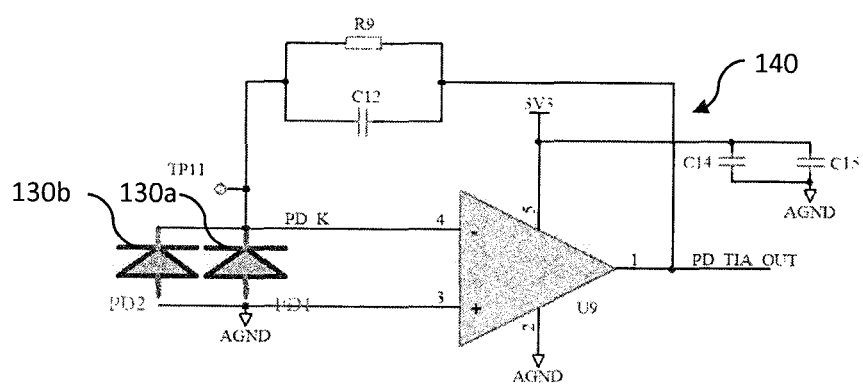
FIG. 7 is a circuit diagram of a transimpedance amplifier associated with the photodetectors of the apparatus of FIG. 1.
Figure 8:
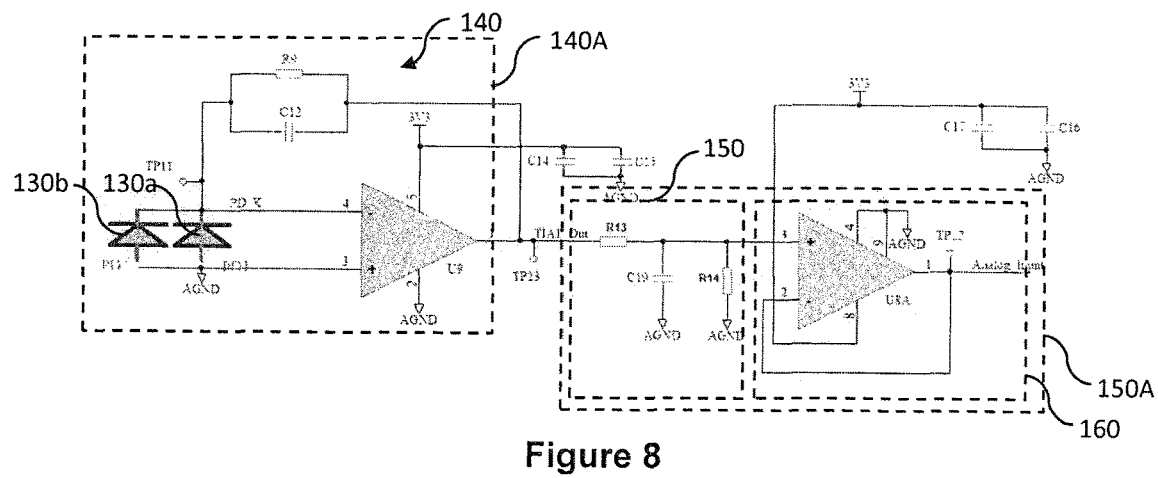
FIG. 8 is a circuit diagram showing one portion of the apparatus of FIG. 1, including a low-pass filter and an associated voltage follower.

FIG. 8 shows a circuit representation of the photodetectors 130, the TIA 140, the first LPF 150 and the voltage follower 160. In this embodiment, the photodetectors 130 include first and second photodetectors 130a, 130b as depicted in FIGS. 6 to 9. The photodetectors 130 are operable to detect a reflection (i.e., a reflected portion) of the light signal to provide a current signal. When the apparatus 100 is worn on the wrist portion, the LED 110 emits the light signal toward the wrist portion and the photodetectors 130a, 130b detect the reflection of the light signal from the wrist portion.

The signal processing circuit is operable to process the current signal into a PPG signal. More specifically, the signal processing circuit is configured to provide a passband of 0.6 Hz to 8 Hz for filtering a voltage signal relating to the current signal so as to provide the PPG signal.

The TIA 140, in this embodiment, is associated with the photodetectors 130a, 130b to form a detector sub-circuit 140A, and is operable to convert the current signal provided by the photodetectors 130a, 130b into the voltage signal. FIG. 7 shows a circuit diagram of the TIA 140 in association with the photodetectors 130a, 130b.

The first LPF 150 is operable to filter (e.g., elimination or suppression) frequency components of the voltage signal above a predetermined cut-off frequency typically ranging from 100 Hz (6000 bpm) to 2000 Hz (120,000 bpm) so as to output a first filtered signal. In this embodiment, the cut-off frequency of the first LPF 150 is 2000 Hz. The first LPF 150 is used for filtering high frequency noise which keeps information pertaining to a toggling signal (range between 80 to 100 Hz) before signal amplification. In other words, if an LPF with a cut-off frequency of 8 Hz were used in place of the first LPF 150, the signal processing circuit would be unable to respond to the toggling signal. After the signal is amplified, it is then possible to obtain a proper PPG signal amplitude. To this end, a 8 Hz LPF (discussed below) can be used to remove noise components of exceeding 8 Hz in frequency in order to improve the SNR of the resultant a PPG signal.

Figure 9:
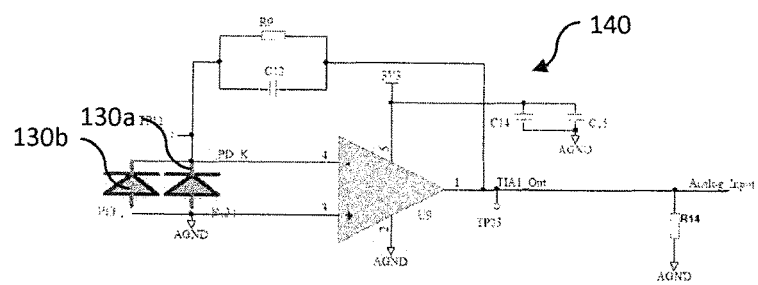
FIG. 9 is a circuit diagram of a modification of the apparatus of FIG. 1 without the low-pass filter and the voltage follower.

The voltage follower 160, as shown in the circuit diagram of FIG. 8, is operable to receive the first filtered signal provided by the first LPF150, and to provide a first intermediate signal. The voltage follower 160 is configured to ensure that its voltage output (i.e., the first intermediate signal) follows its input voltage (i.e., the first filtered signal). This is achieved in the present embodiment through the voltage follower 160 communicating with the TIA 140. The voltage follower 160 includes a non-inverting unity operational amplifier. The first LPF 150 and the voltage follower 160 may not be needed in some embodiments, as shown in FIG. 9. The first LPF 150 and the voltage follower 160 cooperate to provide an active LPF 150A (see, for example, FIG. 2).

The HPF 170 (e.g., a $1^{st}$ order active high pass filter) is operable to filter frequency components of the first intermediate signal below a predetermined cut-off frequency typically ranging from 0.6 Hz (36 bpm) to 0.8 Hz (48 bpm) so as to provide a second filtered signal. In this embodiment, the cut-off frequency of the HPF 170 is 0.6 Hz.

Next, the amplifier 180 is operable to amplify the second filtered signal with a gain value selected from 75 and 150 so as to provide a second intermediate signal. The gain value may be otherwise in other embodiments.

The second LPF 190 (e.g., a passive low pass filter) is operable to filter frequency components of the second intermediate signal below a predetermined cut-off frequency typically ranging from 7.5 Hz (450 bpm) to 8 Hz (480 bpm) so as to provide a third filtered signal. In this embodiment, the cut-off frequency of the second LPF 190 is 8 Hz. The third filtered signal serves as the PPG signal. The HPF 170 and the LPF 190 cooperate to provide the passband.

Figure 3:
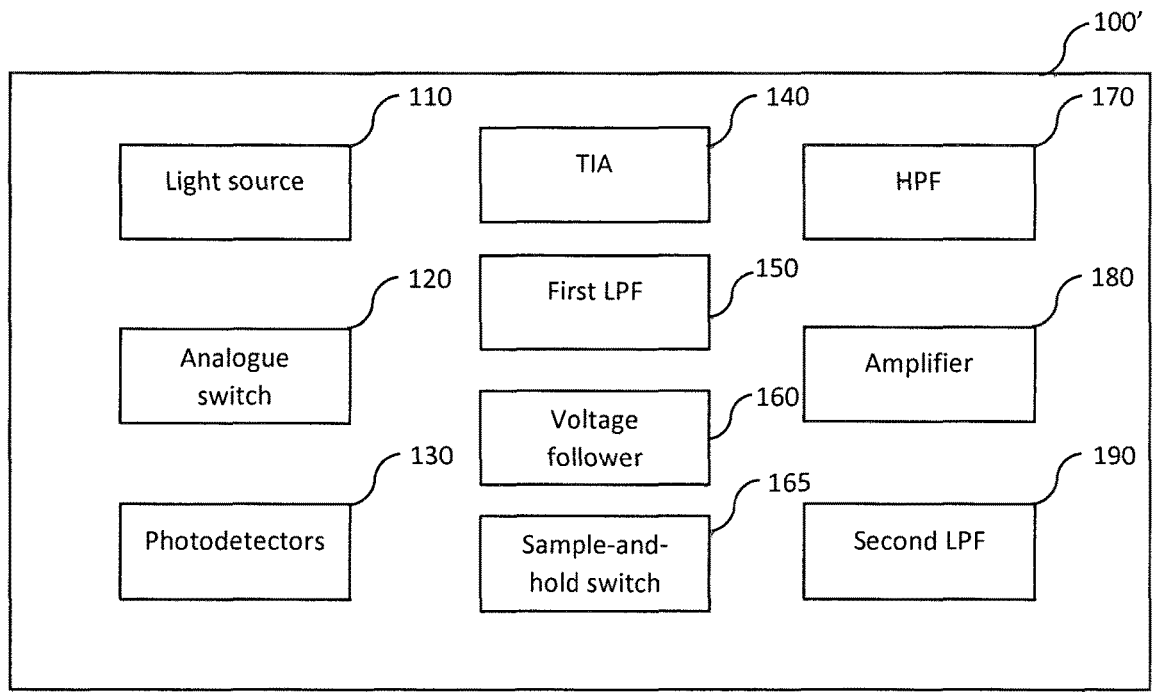
FIG. 3 is a system block diagram of a photoplethysmography (PPG) apparatus for determining physiological changes according another embodiment of the present invention.
Figure 4:
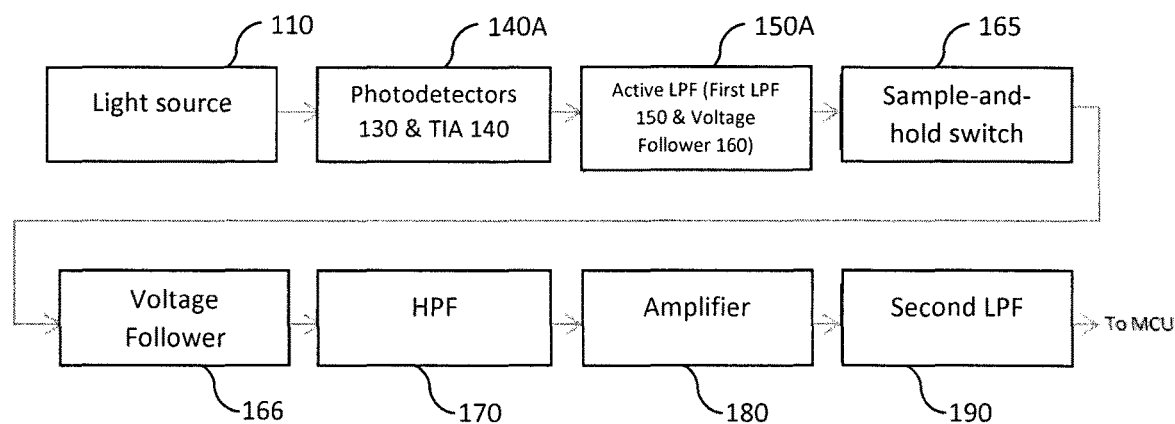
FIG. 4 is a flowchart of signal communication among components of the apparatus of FIG. 3.
Figure 10:
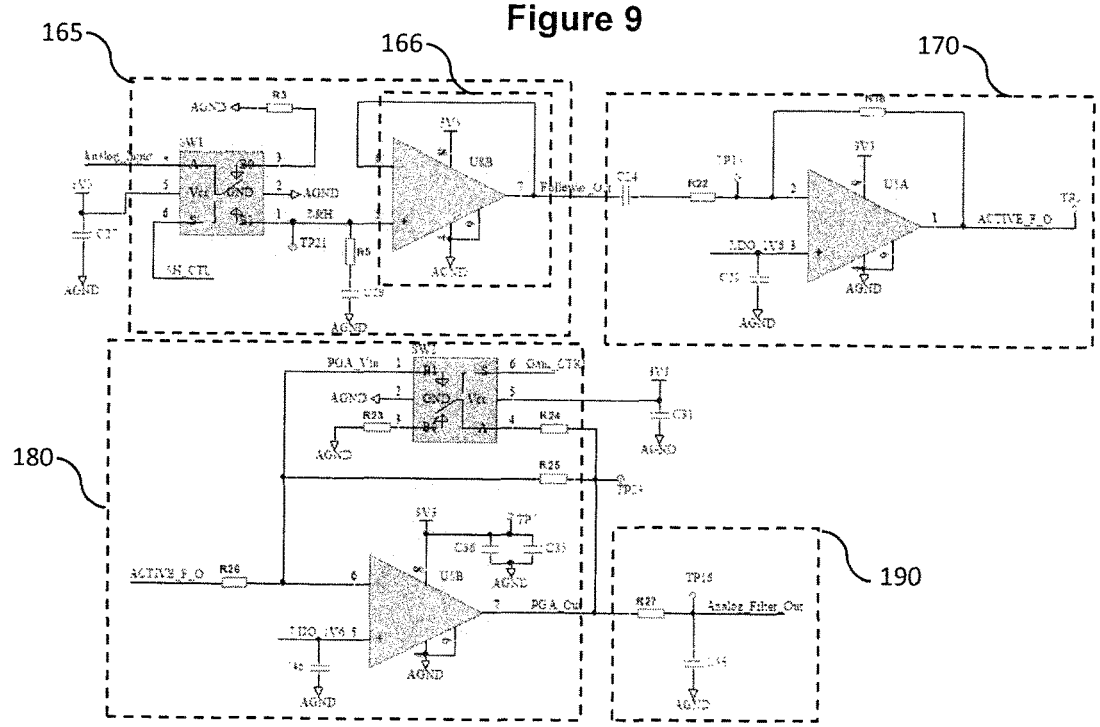
FIG. 10 shows a circuit diagram of a portion of the apparatus of FIG. 3, including a sample-and-hold switch.

FIG. 3 shows a system block diagram of a photoplethysmography apparatus 100' for determining physiological changes according to another embodiment of the present invention. Referring to FIG. 10, the apparatus 100' differs from the apparatus 100 of FIG. 1 in that the apparatus 100' further includes a sample-and-hold switch 165 and another voltage follower 166. The sample-and-hold switch 165 precedes the voltage follower 166 for reducing voltage fluctuation of the LED 110 during the toggling operation of the LED 110. The voltage follower 166 may be considered to form part of the sample-and-hold switch 165. The sample-and-hold switch 165 may be implemented in conjunction with or in place of the analogue switch 120, depending on implementation. An output of the circuit of FIG. 8, marked as "Analog_Input", is received by the circuit of FIG. 10. FIG. 4 illustrates an example flow of signal communication among the components 110-190 of the apparatus 100'.

It should be noted that the apparatus 100, 100' may include other voltage followers or omit some or all of the voltage followers 160, 166. For example, in embodiments without the sample-and-hold switch 165, the voltage follower 166 may be omitted. A skilled reader would understand that at least one voltage follower may be employed by the apparatus 100, 100' in any appropriate manner for voltage maintenance without any amplification effect. As alluded to above, the apparatus 100,100' may not have a voltage follower.

Figure 11A:
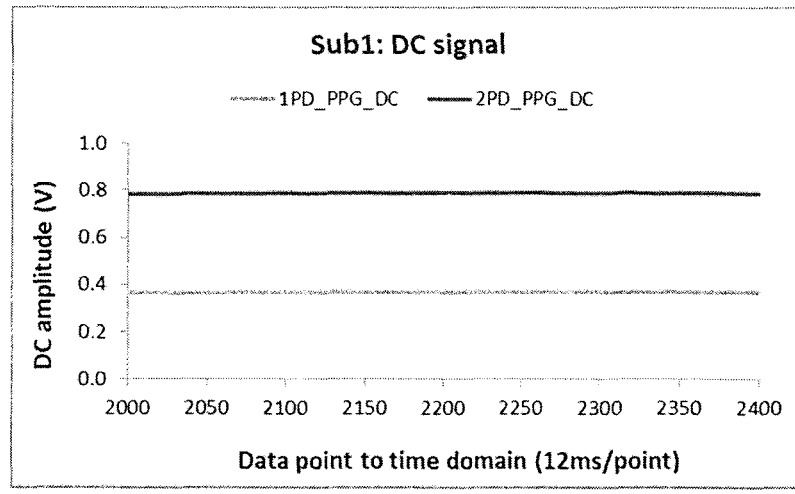
FIGS. 11(a) to 11(c) show a line chart of amplitude versus time for a DC signal.
Figure 11B:
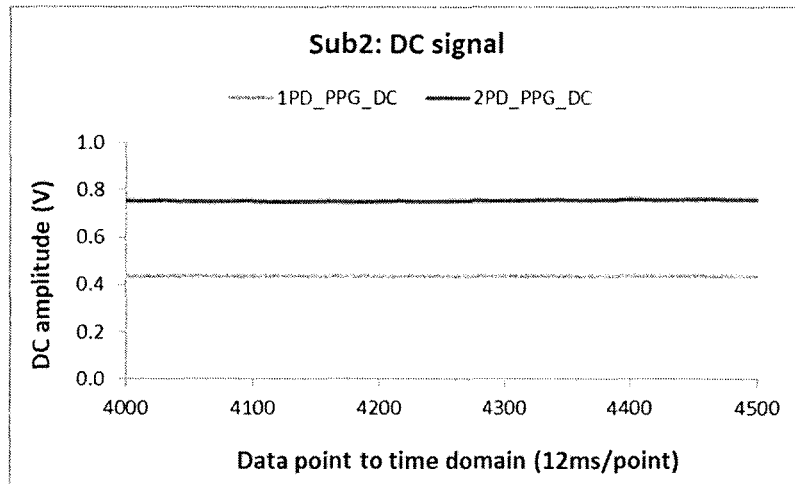
Figure 11C:
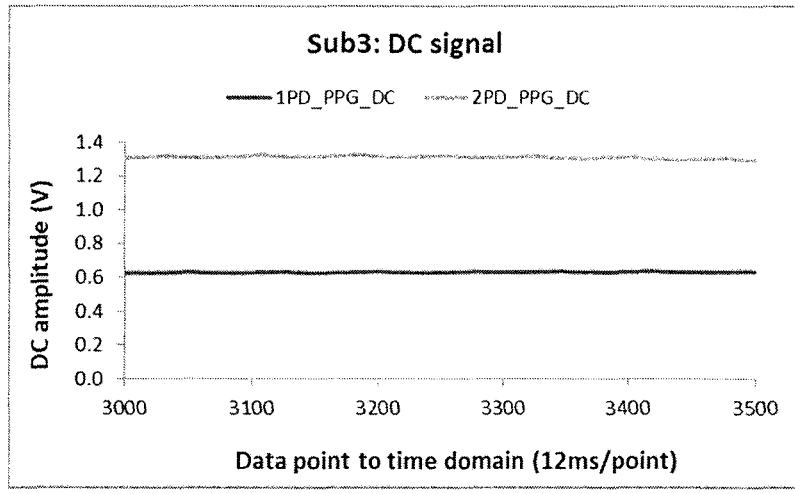
Figure 12A:
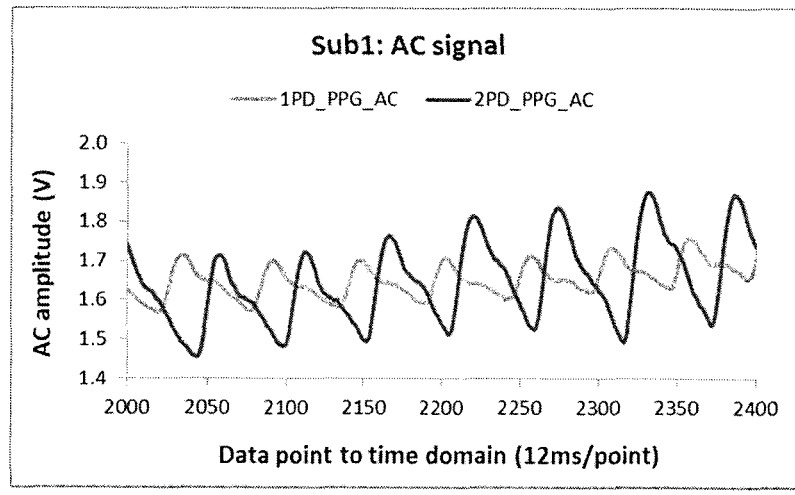
FIGS. 12(a) to 12(c) show a line chart of amplitude versus time for an AC signal.
Figure 12B:
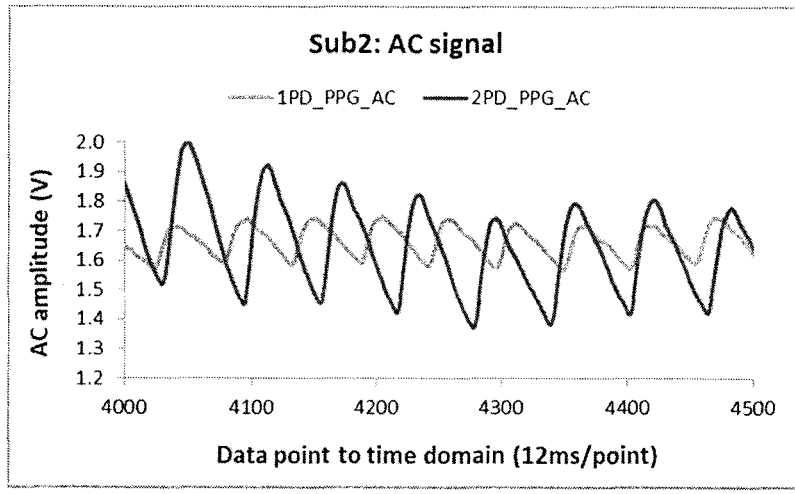
Figure 12C:
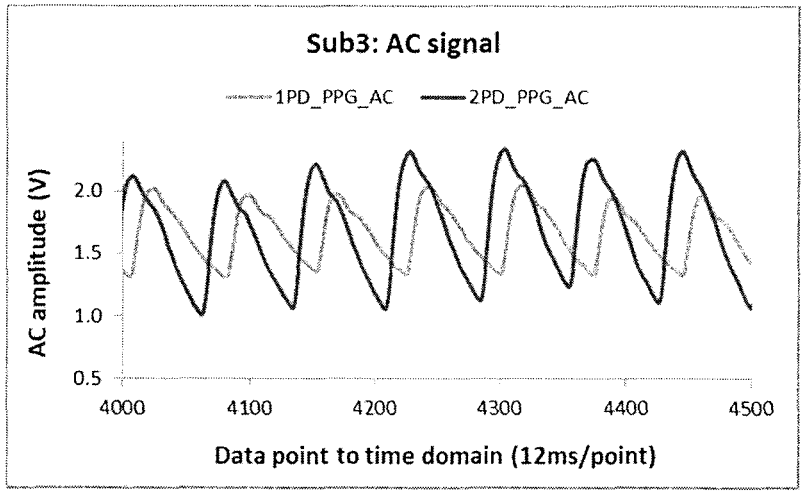
Figure 13:
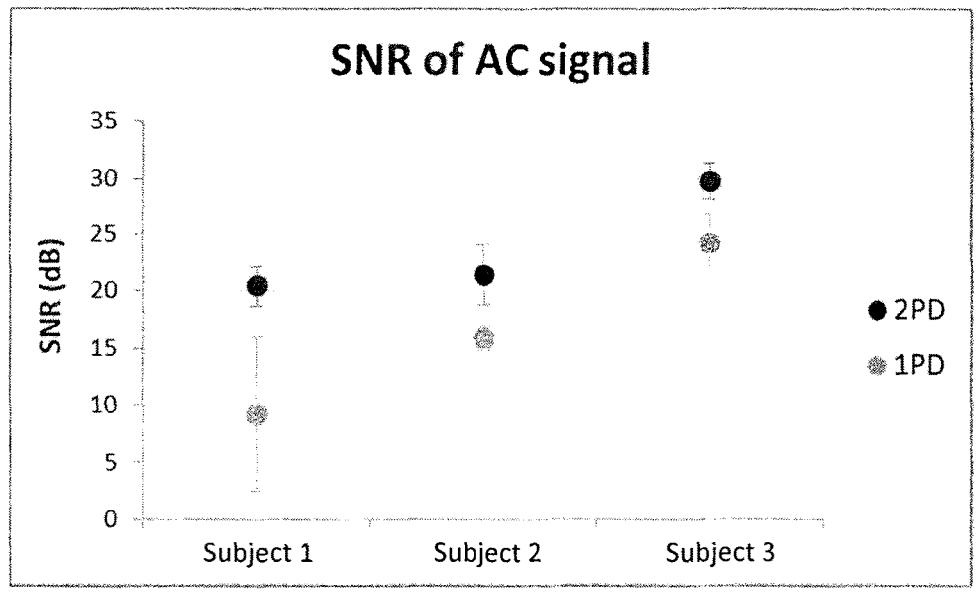
FIG. 13 shows SNR measurements obtained using the apparatus of FIG. 1 and a conventional apparatus for different test subjects.

FIGS. 11(a) to 11(c) show line charts of amplitude versus time for a DC signal during respective time periods. FIGS. 12(a) to 12(c) show line charts of amplitude versus time for an AC signal during respective time periods. FIG. 13 shows signal-to-noise ratios (SNRs) achieved using the photodetectors 130 in comparison with SNRs achieved using a conventional arrangement with a single photodetector, with respect to three test subjects. It can be appreciated that the use of the two photodetectors 130a, 130b results in a significant improvement in SNR.

Figure 14:
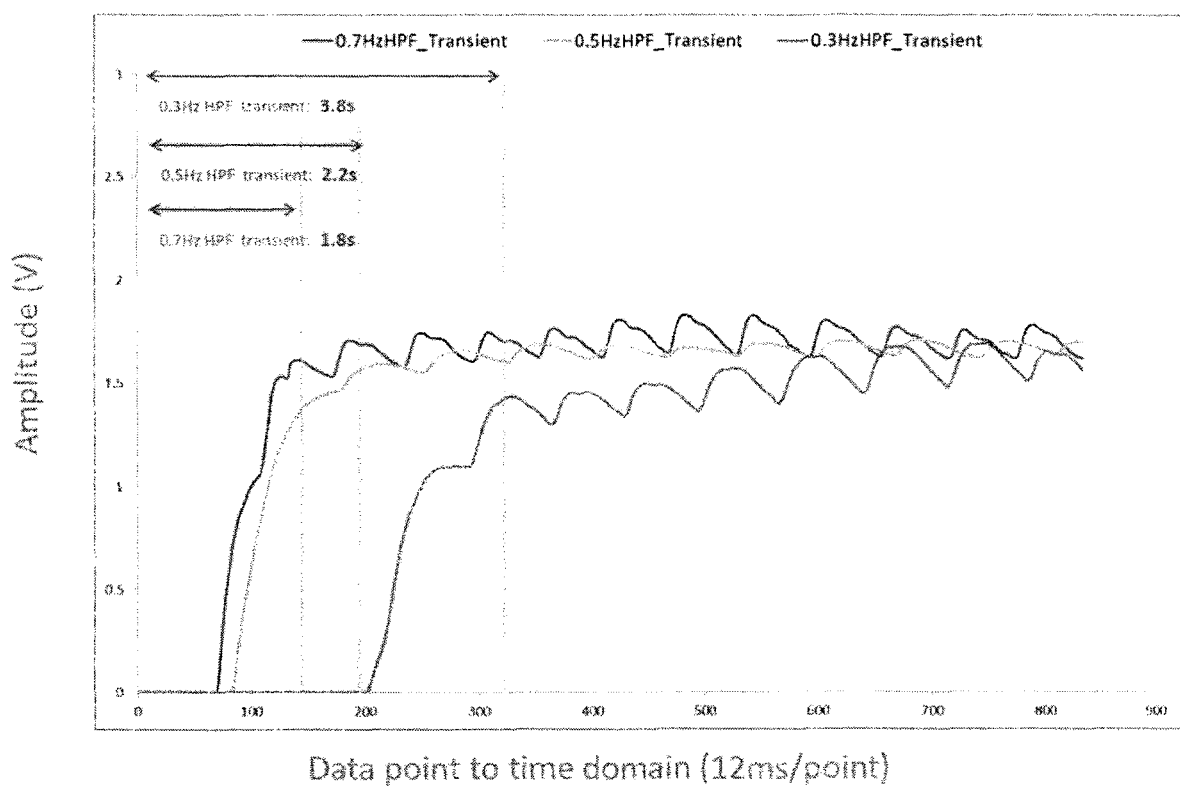
FIG. 14 shows measurements of transient response obtained for a signal processing circuit of the apparatus of FIG. 1.

FIG. 14 shows measurements of transient response obtained for the HPF 170 with the cut-off frequencies set to 0.3 Hz, 0.5 Hz, and 0.7 Hz, respectively. It can be appreciated that DC and other lower frequency components can be quickly removed with the cut-off frequency set to 0.7 Hz, achieving a quicker response characteristic for the signal processing circuit (transient).

Figure 16A:
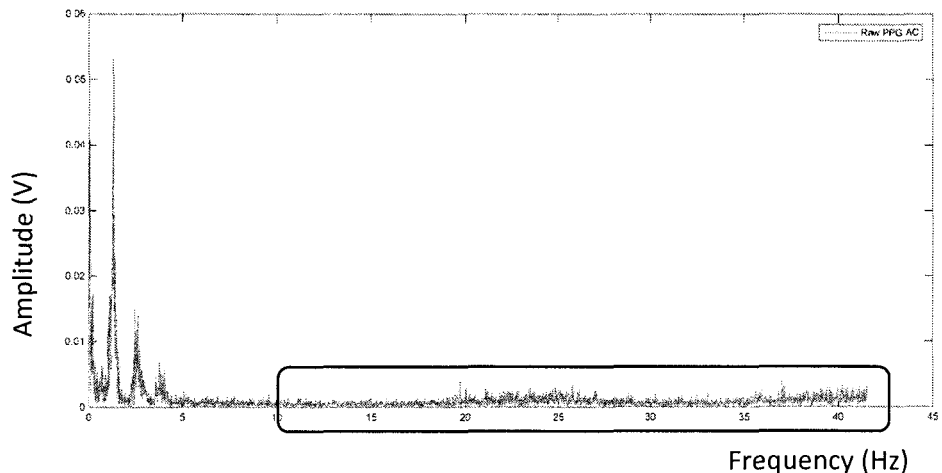
FIGS. 16(a) and 16(b) show frequency-domain (FFT) measurements of the PPG signal of FIG. 15 without and with the LPF, respectively.
Figure 16B:
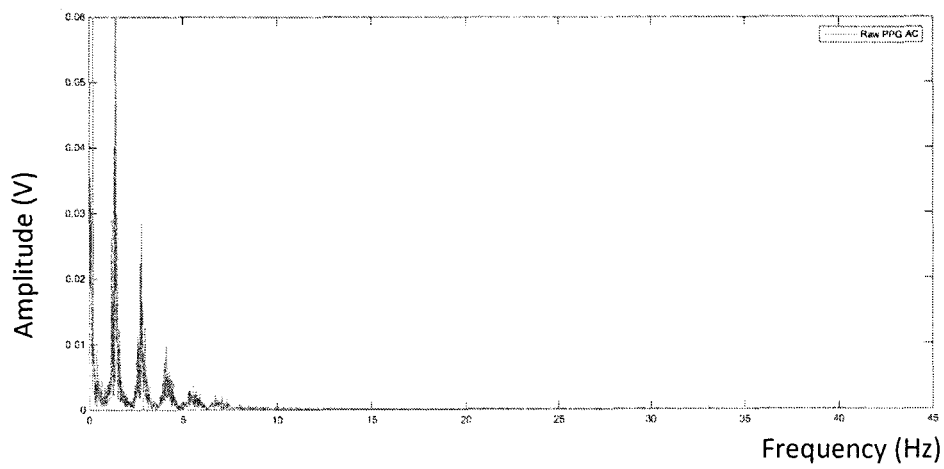

FIGS. 15(a) and 15(b) show time-domain measurements of the PPG signal without and with the second LPF 190, respectively. FIGS. 16(a) and 16(b) show frequency-domain (FFT) measurements of the PPG signal without and with the second LPF 190, respectively. A skilled person would appreciate that frequency components higher than 8 Hz and lower than 0.6 Hz, which may be regarded as noise components, are effectively removed or suppressed by the second LPF 190. Frequency components exceeding 8 Hz and subject to the removal are marked in FIG. 16(a) by a rectangular box. With the noise components removed, the resultant PPG signal includes only frequency components that are particularly relevant to addressing one or more of the technical problems.

Other alternative arrangements are described below.

The filters 150, 170, 190 may be replaced by a suitable filtering circuit configured to provide a passband of 0.6 Hz to 8 Hz. The filter circuit may have non-inverting and inverting operational amplifiers.

The term "provide" and its derivatives as used herein may mean "generate" and its derivatives.

The invention claimed is:

1. A photoplethysmography (PPG) apparatus for determining physiological changes, comprising:
   a light source configured to emit a light signal of one wavelength towards a user's skin, the light signal controlled by a driving current to have a variable intensity level dependent on a skin characteristic of the user's skin;
   a driving circuit including a signal transistor having a base current for controlling the driving current to alternate the light signal between two ON states and one OFF state, at a frequency of greater than 80 Hz, the two ON states corresponding to two different positive intensity levels of the light signal of the same wavelength for two different skin characteristics;
   first and second photodetectors connected in parallel and configured to detect a reflection of the light signal from the user's skin to provide a combined current signal; and
   a signal processing circuit operable to convert the combined current signal into a PPG signal for determining the physiological changes.

2. The apparatus of claim 1, wherein the driving current ranges from 13 mA to 20 mA.

3. The apparatus of claim 1, wherein the light source is operable to alternate between two ON states and an OFF state to emit the light signal, the two ON states corresponding to the two different positive intensity levels of the light signal.

4. The apparatus of claim 1, wherein the signal processing circuit is configured to provide a passband of 0.6 Hz to 8 Hz for filtering a voltage signal relating to the combined current signal so as to provide the PPG signal and wherein the signal processing circuit includes a high-pass filter (HPF) and a second low-pass filter (LPF) cooperating to provide the passband.

5. The apparatus of claim 4, wherein the signal processing circuit further includes a first LPF with a cut-off frequency ranging from 100 Hz to 2000 Hz.

6. The apparatus of claim 5, wherein the signal processing circuit further includes a voltage follower arranged between the HPF and the first LPF.

7. The apparatus of claim 5, wherein the signal processing circuit further includes an amplifier arranged between the HPF and the first LPF.

8. The apparatus of claim 1, the signal processing circuit comprising:
   a first signal processor configured to provide a command from a microcontroller unit (MCU) port to a digital-to-analog convertor to communicate with the driving circuit;
   a second signal processor configured to convert the combined current signal to a voltage signal; and
   a third signal processor configured to provide a cut-off frequency.

9. The apparatus of claim 8, further comprising at least one voltage follower configured to communicate with the second signal processor to maintain a voltage output level.

10. The apparatus of claim 9, wherein the at least one voltage follower communicates with at least one gain amplifier, wherein the at least one gain amplifier further communicates with the third signal processor to amplify to a desired gain.

11. The apparatus of claim 10, wherein the desired gain is 75 or 150.

12. The apparatus of claim 8, wherein the cut-off frequency is from 0.6 Hz to 8.0 Hz.

13. The apparatus of claim 12, wherein the third signal processor is a band pass filter.

14. The apparatus of claim 1, wherein the light source is green color.

15. The apparatus of claim 1, the photodetectors comprising only the first and second photodetectors.

16. A photoplethysmography (PPG) method for determining physiological changes, comprising:
   emitting, using a light source, a light signal of one wavelength towards a user's skin, the light signal controlled by a driving current to have a variable intensity level dependent on a skin characteristic of the user's skin;
   controlling, using a driving circuit including a signal transistor having a base current, the driving current to alternate the light signal between two ON states and one OFF state, at a frequency of greater than 80 Hz, the two ON states corresponding to two different positive intensity levels of the light signal of the same wavelength for two different skin characteristics;
   detecting, using first and second photodetectors connected in parallel, a reflection of the light signal from the user's skin to provide a combined current signal; and
   converting, using a signal processing circuit, the combined current signal into a PPG signal for determining the physiological changes.

17. The method of claim 16, comprising:
   converting the combined current signal to a voltage signal, wherein an analog signal of the voltage signal is processed to amplify and filter the analog signal.

18. The method of claim 17, further comprising maintaining a voltage output level of the voltage signal with at least one voltage follower.

19. The method of claim 18, wherein the at least one voltage follower communicates with at least one gain amplifier, amplifying a desired gain with the at least one gain amplifier.

20. The method of claim 17, wherein the converting of the combined current signal to the voltage signal is based on a transimpedance amplifier.

* * * * *